US006315724B1

(12) United States Patent
Berman et al.

(10) Patent No.: US 6,315,724 B1
(45) Date of Patent: Nov. 13, 2001

(54) 3-DIMENSIONAL ULTRASONIC IMAGING

(75) Inventors: Michael Berman, Har Adar (IL); James Gessert, Colorado Springs; Wayne Moore, Lyons, both of CO (US); Rachel Nechushtai, Motza Elit (IL); Hillel Rom, Bet Zait (IL); Ziv Soferman, Givatayim (IL)

(73) Assignee: Biomedicom LTD, Jerusalem (IL)

( * ) Notice: Subject to any disclaimer, the term of this patent is extended or adjusted under 35 U.S.C. 154(b) by 0 days.

(21) Appl. No.: 09/421,046

(22) Filed: Oct. 19, 1999

(51) Int. Cl.[7] .................................................. A61B 8/00
(52) U.S. Cl. .......................... 600/443; 128/916; 600/459
(58) Field of Search .................................. 600/437, 443, 600/447, 459; 128/916

(56) References Cited

U.S. PATENT DOCUMENTS

| 4,458,536 | 7/1984 | Ahn et al. ................................ 73/652 |
| 4,930,365 | 6/1990 | Porat et al. .............................. 74/5.6 |
| 4,932,414 | 6/1990 | Coleman et al. ................ 128/660.09 |
| 5,039,035 | 8/1991 | Fitzpatrick ............................ 224/122 |
| 5,071,160 | 12/1991 | White et al. ........................ 280/735 |
| 5,398,691 | 3/1995 | Martin et al. ................... 128/662.06 |
| 5,764,014 | 6/1998 | Jakeway et al. ..................... 318/587 |
| 5,817,022 | 10/1998 | Vesely .................................. 600/443 |
| 5,836,869 | 11/1998 | Kudo et al. .......................... 600/173 |
| 5,875,257 | 2/1999 | Marrin et al. ........................ 382/107 |

OTHER PUBLICATIONS

"Efficient Ray Tracing of Volume Data", M. Levoy, ACM Transactions on Graphics, vol. 9, No. 3, pp. 245–261, 1990.
AC3C61—"Curved Array General Imaging Scanhead", Specifications, Acoustic Research Systems, Inc., Longmont, Colorado, 1999.
Sonora Medical Systems, "RT 3200 Advantage II Ultrasound System for Obstetrics and Gynecology", 1999.
Rafael "Two–Axis Angular–Rate Gyro—System Description", Haifa, Israel.

*Primary Examiner*—Francis J Jaworski
(74) *Attorney, Agent, or Firm*—Abelman, Frayne & Schwab (57) ABSTRACT

An ultrasonic imaging system including a probe containing at least one ultrasonic transducer and at least one inertial sensor as well as electronic circuitry connected to the probe for causing the at least one ultrasonic transducer to transmit ultrasonic energy into a region and to receive reflected ultrasonic energy therefrom, creating a plurality of generally two-dimensional images whose geometrical relationship is indicated by outputs from the at least one inertial sensor.

35 Claims, 10 Drawing Sheets

3-DIMENSIONAL ULTRASONIC IMAGING

FIELD OF THE INVENTION

The present invention relates to ultrasonic imaging generally and more particularly to three-dimensional ultrasonic imaging using conventional two-dimensional ultrasonic imaging apparatus.

BACKGROUND OF THE INVENTION

There exists a variety of two-dimensional ultrasonic imaging apparatus. Such apparatus is used in various medical disciplines, such as cardiology, radiology and obstetrics. In the field of obstetrics, apparatus having a very large installed base in the U.S.A. is the General Electric Model GE-3200. Other two-dimensional ultrasonic imaging apparatus is commercially available inter alia from ATL, a subsidiary of Phillips, Acuson, Toshiba Ultrasound, Siemens Ultrasound and Hewlett-Packard Ultrasound.

Three-dimensional ultrasonic imaging apparatus is also known and commercially available from 3-D Ultrasound Inc. of North Carolina, U.S.A.

Various mechanisms have been employed in an attempt to retrofit conventional two-dimensional ultrasonic imaging apparatus for use in providing three-dimensional ultrasonic images. These include, for example:

mechanical assemblies which constrain the motion of the ultrasonic probe and measure its position using rotary position encoders;

electromagnetic position sensors which require an external field generator in the vicinity of the patient;

optical position sensors which require mounting of cameras in the vicinity of the patient;

acoustic position sensors which require transducers to be mounted onto the patient; and motor assemblies which move at least part of the probe at a constant rate which allows image position and orientation to have a fixed relationship to timing.

The following U.S. Patents are believed to be relevant to the general field of the present invention: U.S. Pat. Nos. 5,817,022; 5,398,691; and 4,932,414.

SUMMARY OF THE INVENTION

The present invention seeks to provide an ultrasonic imaging probe and an ultrasonic imaging system which provides three-dimensional imaging and which is characterized by simplicity of construction and operation and relatively low cost. The system may be implemented in original equipment or as a retrofit to existing equipment having only two-dimensional imaging capabilities.

There is thus provided in accordance with a preferred embodiment of the present invention a retrofit ultrasonic imaging system including an ultrasonic imaging system comprising a probe including at least one ultrasonic transducer, and at least one inertial sensor, and electronic circuitry connected to the probe for causing the at least one ultrasonic transducer to transmit ultrasonic energy into a region and to receive reflected ultrasonic energy therefrom, creating a plurality of generally two-dimensional images whose geometrical relationship is indicated by outputs from the at least one inertial sensor.

Further in accordance with a preferred embodiment of the present invention the inertial sensor includes a gyroscope.

Still further in accordance with a preferred embodiment of the present invention the gyroscope is capable of sensing motion having one degree of freedom.

Additionally or alternatively the inertial sensor includes a micro-mechanical device. Furthermore, the inertial sensor may also include a sensor employing the Coriolis force.

Additionally in accordance with a preferred embodiment of the present invention the gyroscope is capable of sensing velocity having one angular degree of freedom.

Further in accordance with a preferred embodiment of the present invention the gyroscope is capable of sensing motion having more than one degree of freedom.

Preferably the micro-mechanical device is capable of sensing motion having one degree of freedom. Additionally the micro-mechanical device is capable of sensing velocity having one angular degree of freedom. Preferably the micro-mechanical device is capable of sensing motion having more than one degree of freedom.

Still further in accordance with a preferred embodiment of the present invention the inertial sensor is capable of sensing motion having one degree of freedom. Additionally the sensor is capable of sensing velocity having one angular degree of freedom. Preferably the sensor is capable of sensing motion having more than one degree of freedom.

Still further in accordance with a preferred embodiment of the present invention the electronic circuitry includes video capture circuitry for capturing individual two-dimensional video images and an image organizer, combining the individual two-dimensional video images into a three-dimensional image based on information from the at least one inertial sensor.

Additionally in accordance with a preferred embodiment of the present invention the electronic circuitry includes video capture circuitry for capturing a time series of two-dimensional video images of a video stream and an image organizer, combining the individual two-dimensional video images into a three-dimensional image based on information from the at least one inertial sensor.

Further in accordance with a preferred embodiment of the present invention the electronic circuitry includes video capture circuitry for capturing individual two-dimensional video images, an image organizer, combining the individual two-dimensional video images into a three-dimensional image based on information from the at least one inertial sensor, and a three-dimensional visualizer receiving an output from the image organizer and providing a human sensible three dimensional image.

Still further in accordance with a preferred embodiment of the present invention the electronic circuitry includes video capture circuitry for capturing a time series of two-dimensional video images of a video stream, an image organizer, combining the individual two-dimensional video images into a three-dimensional image based on information from the at least one inertial sensor, and a three-dimensional visualizer receiving an output from said image organizer and providing a human sensible three dimensional image.

Additionally in accordance with a preferred embodiment of the present invention the electronic circuitry includes circuitry for receiving information representing individual two-dimensional ultrasonic images and combining the individual two-dimensional ultrasonic images into a three-dimensional image based on information from the at least one inertial sensor.

Preferably the electronic circuitry creates the three-dimensional image by interpolating image values from the individual two-dimensional ultrasonic images.

Additionally in accordance with a preferred embodiment of the present invention, the ultrasonic imaging system also includes an operator actuated switch for selectably operating said at least one inertial sensor. Preferably the imaging system also includes an operator sensible indicator indicating operation of the at least one inertial sensor.

There is also provided in accordance with another preferred embodiment of the present invention an ultrasonic imaging system including a probe comprising at least one ultrasonic transducer, and at least one sensor which does not require provision of a reference external thereto, and electronic circuitry connected to the probe for causing the at least one ultrasonic transducer to transmit ultrasonic energy into a region and to receive reflected ultrasonic energy therefrom, creating a plurality of generally two-dimensional images whose geometrical relationship is indicated by outputs from the at least one sensor.

There is further provided in accordance with yet another preferred embodiment of the present invention a probe assembly for use in an ultrasonic imaging system and including at least one ultrasonic transducer, and at least one inertial sensor.

Further in accordance with a preferred embodiment of the present invention the at least one inertial sensor comprises a gyroscope capable of sensing motion having one degree of freedom.

Still further in accordance with a preferred embodiment of the present invention the gyroscope is capable of sensing motion having more than one degree of freedom.

Additionally in accordance with a preferred embodiment of the present invention the probe also includes electronic circuitry creating a plurality of generally two-dimensional images whose geometrical relationship is indicated by outputs from the at least one inertial sensor.

Preferably the electronic circuitry includes video capture circuitry for capturing individual two-dimensional video images, an image organizer, combining the individual two-dimensional video images into a three-dimensional image based on information from said at least one inertial sensor, and a three-dimensional visualizer receiving an output from said image organizer and providing a human sensible three dimensional image.

Further in accordance with a preferred embodiment of the present invention the electronic circuitry includes circuitry for receiving information representing individual two-dimensional ultrasonic images and combining the individual two-dimensional ultrasonic images into a three-dimensional image based on information from the at least one inertial sensor.

Still further in accordance with a preferred embodiment of the present invention the a probe assembly also includes an operator actuated switch for selectably operating the at least one inertial sensor. Preferably the operator sensible indicator indicating operation of said at least one inertial sensor.

There is also provided in accordance with yet another preferred embodiment of the present invention a method for providing ultrasonic imaging including the steps of providing a probe including an ultrasonic transducer and at least one inertial sensor, causing the ultrasonic transducer to transmit ultrasonic energy into a region and to receive reflected ultrasonic energy therefrom, creating a plurality of generally two-dimensional images, and determining a spatial relationship between the plurality of two-dimensional images using outputs from the at least one inertial sensor.

Further in accordance with a preferred embodiment of the present invention the step of causing includes the step of rotating the probe about a generally fixed axis at a location of interest, thereby producing a plurality of generally two dimensional images lying in planes which intersect at the axis and whose relative orientations are known from outputs of the at least one inertial sensor.

Still further in accordance with a preferred embodiment of the present invention the method also includes the steps of capturing individual two-dimensional video images and combining the individual two-dimensional video images into a three-dimensional image based on information from the at least one inertial sensor.

Additionally in accordance with a preferred embodiment of the present invention the method also includes the steps of receiving information representing individual two-dimensional ultrasonic images and combining the individual two-dimensional ultrasonic images into a three-dimensional image based on information from the at least one inertial sensor.

Further in accordance with a preferred embodiment of the present invention the method also includes operator actuation of a switch for selectably operating the at least one inertial sensor. Preferably the method also includes providing a visual indication of operation of said at least one inertial sensor.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

Figure 1:
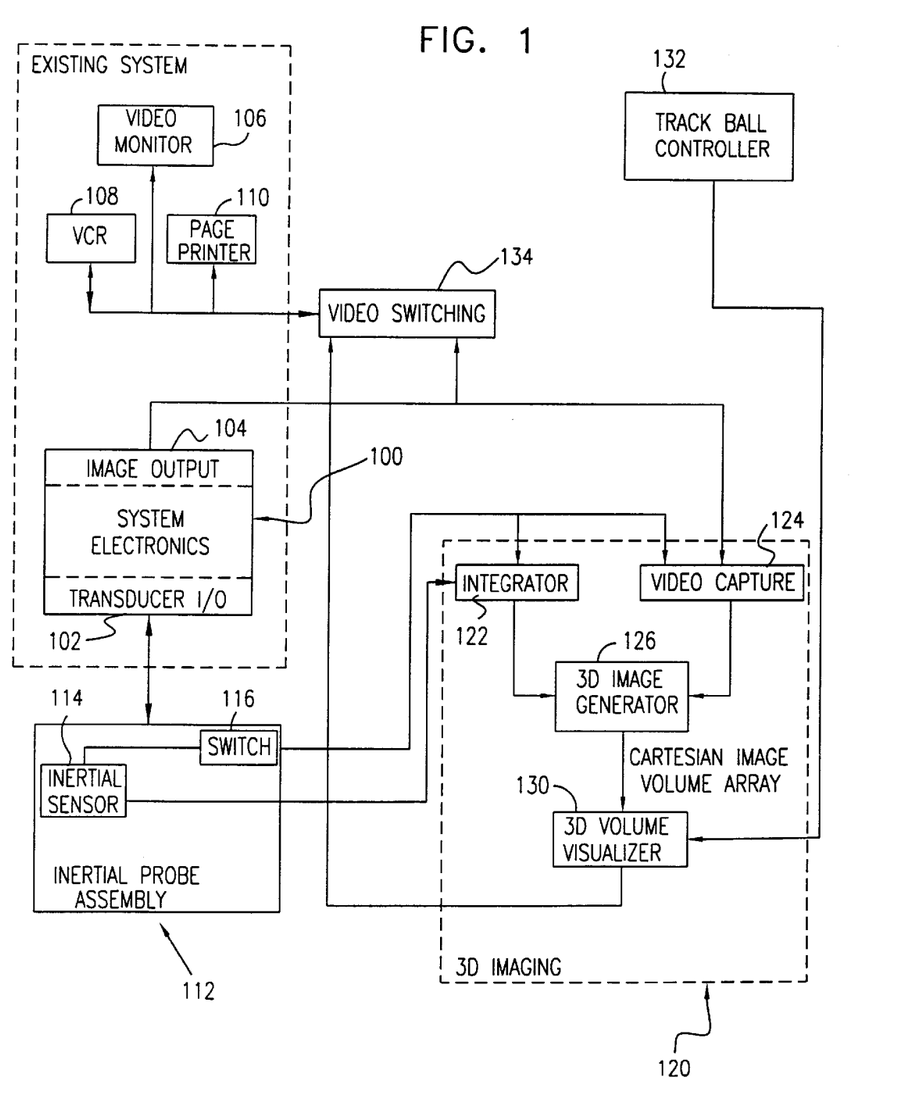
FIG. 1 is a simplified block diagram illustration of a retrofit ultrasonic imaging system constructed and operative in accordance with one preferred embodiment of the present invention.

Reference is now made to FIG. 1, which is a simplified block diagram illustration of an ultrasonic imaging system constructed and operative in accordance with a preferred embodiment of the present invention. The system may be implemented in original equipment or as a retrofit to existing equipment having only two-dimensional imaging capabilities. An example of a retrofit existing system is described hereinbelow with the understanding that the present invention applies equally to a non-retrofit implementation.

As seen in FIG. 1, an existing system, typically a Model GE 3200 manufactured by General Electric Company of the U.S.A. or an UltraMark 4+ or HDI Series, both manufactured by ATL Inc. of Seattle, Wash., U.S.A., is provided and includes conventional system electronics 100, comprising a transducer interface port 102 and an image output port 104. A video monitor 106, a VCR 108 and a page printer 110 are typically coupled to the image output port 104.

In accordance with a preferred embodiment of the present invention, in place of a conventional ultrasonic probe assembly, there is provided and coupled to port 102 an inertial probe assembly 112, constructed and operative in accordance with a preferred embodiment of the present invention. As will be described in greater detail hereinbelow, the inertial probe assembly 112 includes an inertial sensor 114 which is actuated by an operator-controlled switch 116 and typically provides at least an angular velocity output. The switch 116 may be located on the probe, as illustrated. Alternatively it may be located elsewhere in the system.

Additionally in accordance with a preferred embodiment of the present invention there is provided three-dimensional imaging circuitry 120, constructed and operative in accordance with a preferred embodiment of the present invention. Circuitry 120, which is preferably embodied in a combination of hardware and software, typically comprises an integrator 122, which receives the output of inertial sensor 114. Video capture circuitry 124, receives a video image output from image output port 104 of system electronics 100 and an inertial sensor operation indication output from switch 116.

Outputs from integrator 122 and from video capture circuitry 124 are supplied to a 3D image generator 126. In the embodiment of FIGS. 2–7, wherein the inertial sensor 114 is typically a tracker operative to sense motion having one degree of freedom, the 3D image generator 126 is operative to synchronize various two-dimensional images captured by circuitry 124 during a rotational sweep carried out by the probe assembly 112 about a fixed axis.

The output of 3D image generator 126 is supplied to a 3D volume visualizer 130, which may receive an optional input from a track ball controller 132 or other suitable input device and provides an output to video switching circuitry 134. The output of 3D image generator 126 may also be employed to carry out various measurements. Video switching circuitry 134 also receives a video image output from system electronics 100 via image output port 104 and provides outputs to the video monitor 106, VCR 108 and page printer 110. Video switching circuitry 134 may also provide switching of outputs of the VCR 108 to the video monitor 106.

Figure 2:
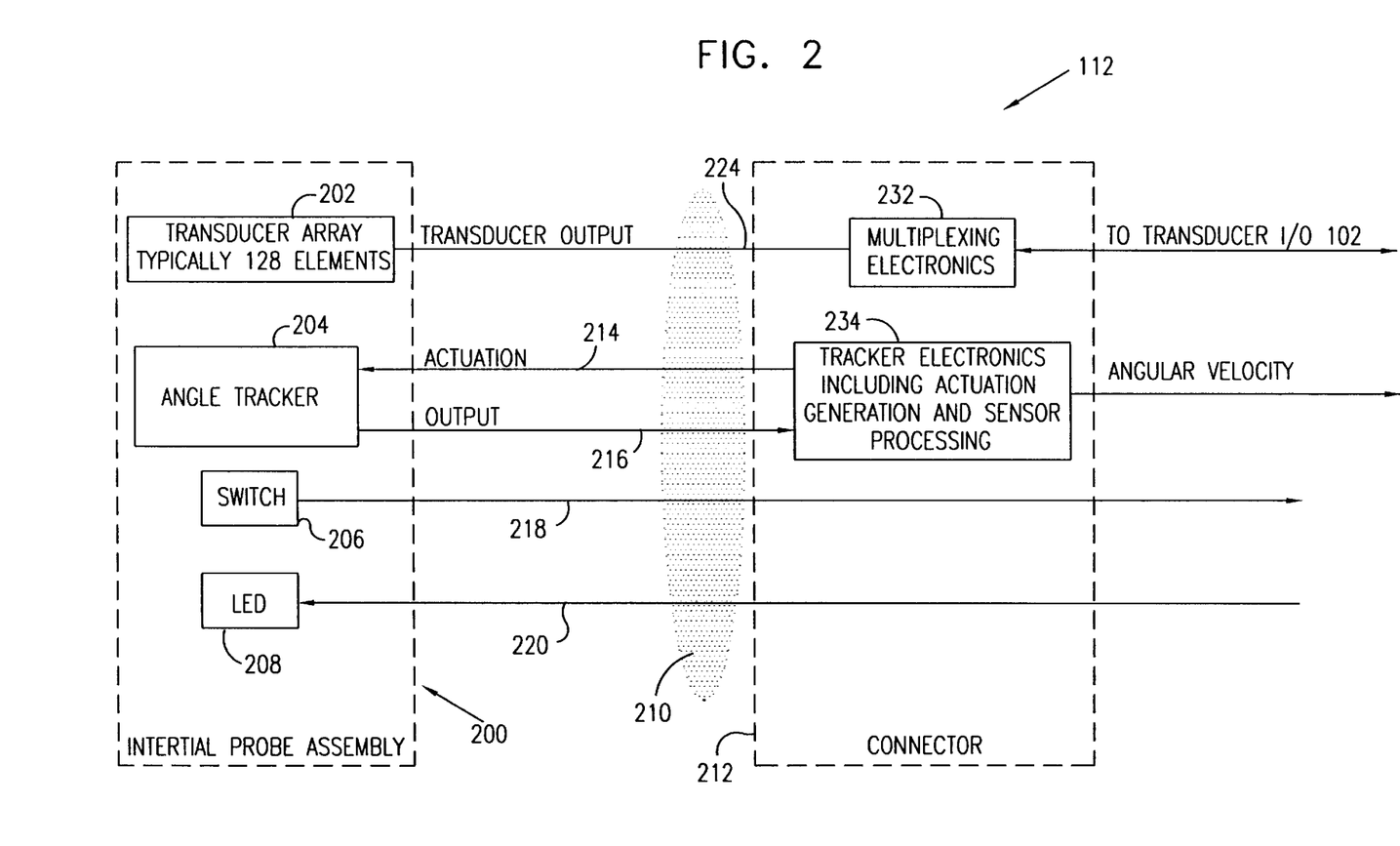
FIG. 2 is a simplified block diagram illustration of a probe assembly forming part of the embodiment of FIG. 1.

Reference is now made to FIG. 2, which is a simplified block diagram illustration of a preferred structure of a probe assembly 112 forming part of the system of FIG. 1 in accordance with one embodiment of the present invention. The probe assembly of FIG. 2 preferably includes a transducer housing 200 within which is located a conventional ultrasonic transducer array 202, such as a 128 element array which is commercially available from Sonora Medical Systems, Inc. of Longmont, Colo.

In accordance with a preferred embodiment of the present invention, there is also provided within the transducer housing 200 an angle tracker 204, such as a Two-Axis Angular-Rate Gyro (TAARG) commercially available from Rafael of Israel and described in U.S. Pat. No. 4,930,365, the disclosure of which is hereby incorporated by reference. Angle tracker 204 corresponds to inertial sensor 114 (FIG. 1). Additionally located within the transducer housing 200 there may be provided a manually operable ON-OFF switch 206, which corresponds to switch 116 (FIG. 1). Preferably, a LED 208 is associated with switch 206, to indicate when the system is ready for data acquisition and thus that information provided by the angle tracker 204 is being acquired. Alternatively, the LED 208 may be located elsewhere in the system or any other suitable type of indicator may be provided.

The transducer housing 200 and its internal components are coupled via a connector cable 210 to a multifunctional connector 212. The multifunctional connector 212 is illustrated in FIG. 3 and the cable 210 is illustrated in section in FIG. 4.

Figure 3:
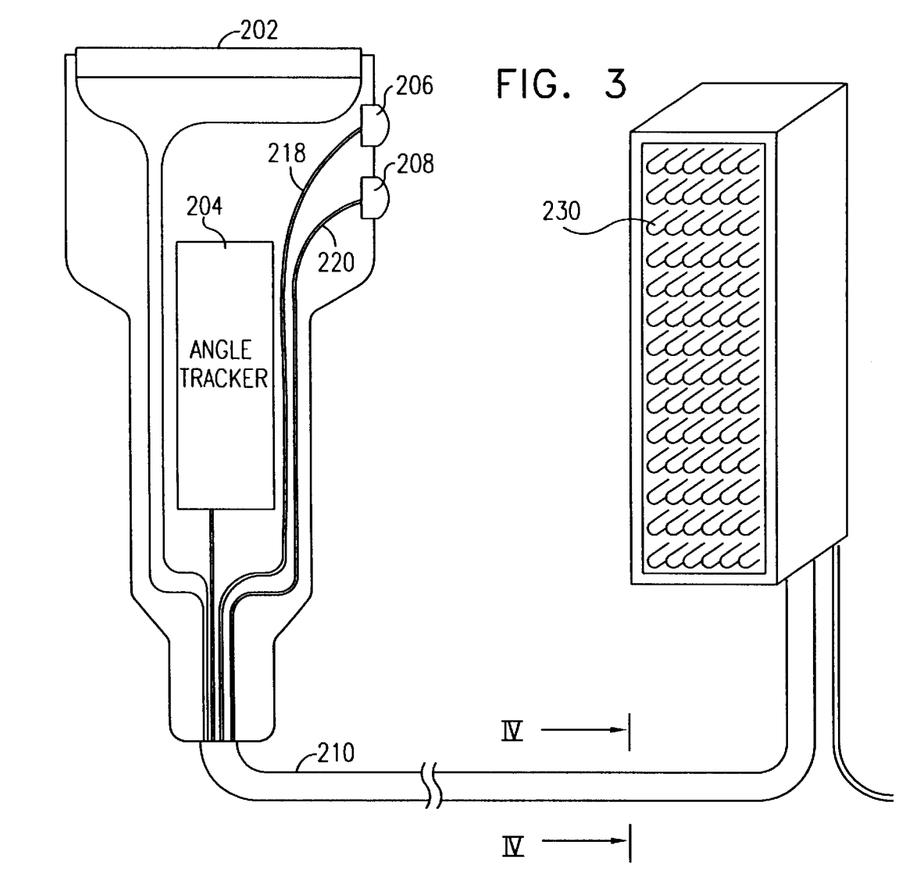
FIG. 3 is a simplified pictorial illustration of the probe assembly of FIG. 2.
Figure 4:
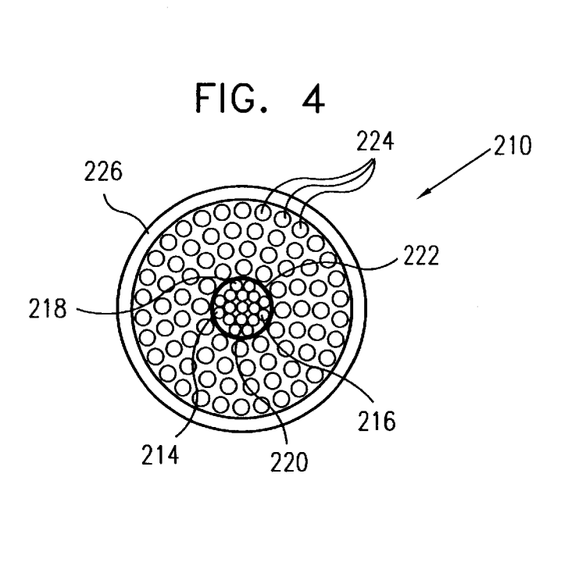
FIG. 4 is a sectional illustration of a coaxial cable forming part of the probe assembly of FIG. 3, taken along lines IV—IV in FIG. 3.

As seen in FIGS. 2–4, the connector cable 210 preferably includes at the interior thereof angle tracker actuation and output cables 214 and 216 as well as a switch status cable 218 and a LED actuation cable 220. These cables are surrounded by a shield 222 and outwardly thereof by a collection of typically 128 transducer output cables 224 and by an outer cable shield 226. Where the switch 116 and LED 208 are not part of the probe assembly 112, cables 218 and 220 may be obviated in the connector cable 210.

Multifunctional connector 212 typically includes a 156 pin array 230, as seen in FIG. 3, which is preferably plug compatible with conventional transducer interface ports 102 of conventional system electronics 100 of conventional ultrasonic imaging systems such as Model GE 3200 manufactured by General Electric Company of the U.S.A. or an UltraMark 4+, manufactured by ATL Inc. of Seattle, Wash., U.S.A.

As seen in FIG. 2, multifunctional connector 212 may include multiplexing electronics 232 which is usually employed in connectors which are conventionally connected to conventional transducer interface ports 102 of conventional system electronics 100 of some conventional ultrasonic imaging systems such as Model GE 3200 manufactured by General Electric company of the U.S.A.

Multifunctional connector 212 preferably also includes tracker electronics 234 including actuation generation and sensor processing. Tracker electronics 234 suitable for use with angle tracker 204 is commercially available from Rafael of Israel, as part of the Two-Axis Angular-Rate Gyro (TAARG), described in U.S. Pat. No. 4,930,365. The output of tracker electronics 234 is preferably the angular velocity output which is supplied to integrator 122.

Figure 5:
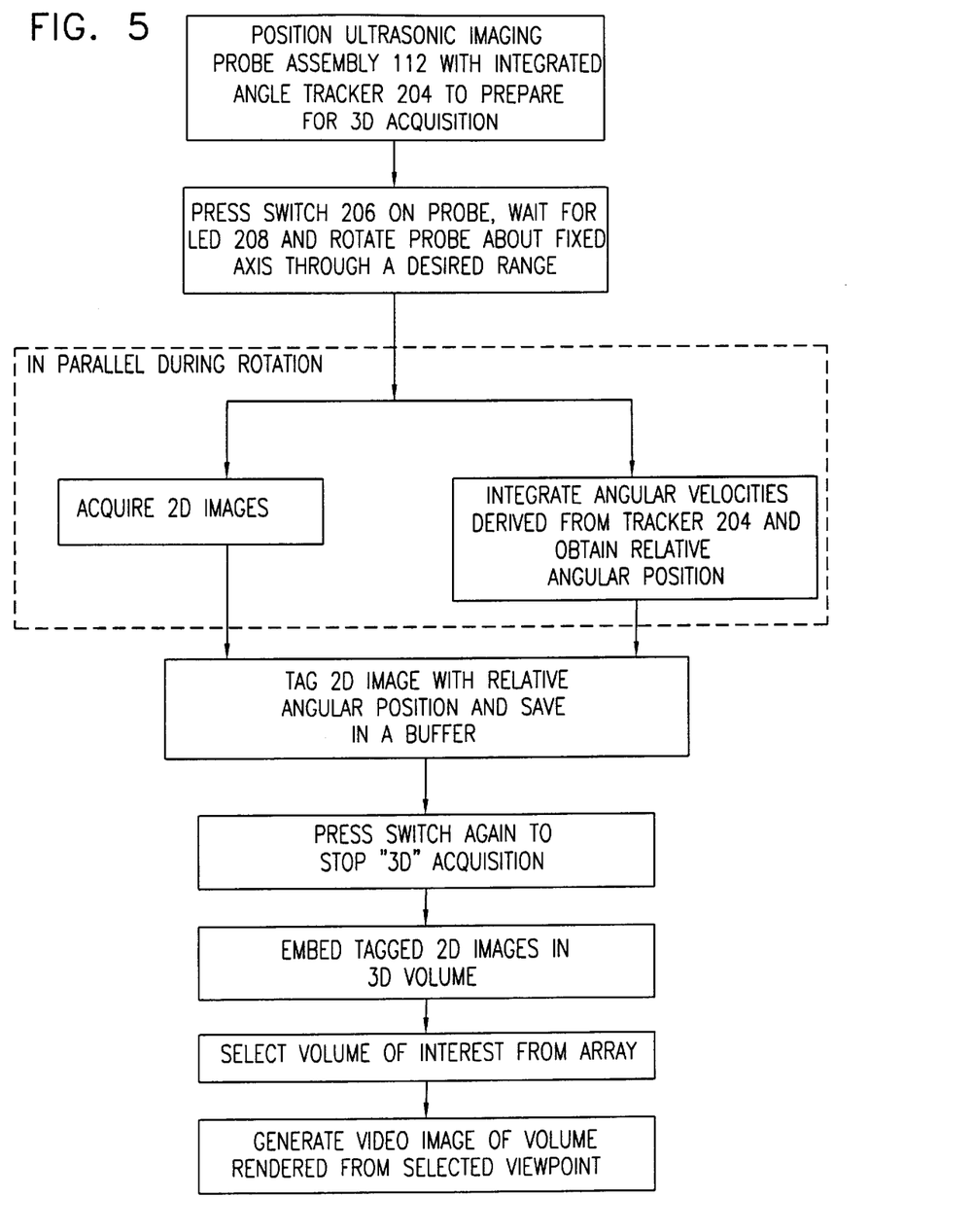
FIG. 5 is a simplified flow chart illustration of three-dimensional data acquisition in the embodiment of FIGS. 1–4.

Reference is now made to FIG. 5, which is a simplified flow chart illustration of three-dimensional data acquisition in the embodiment of FIGS. 1–4. Initially, the inertial probe assembly 112 (FIG. 1) including angle tracker 204 (FIG. 2) is positioned by an operator relative to a patient for 3 dimensional image acquisition.

The operator then actuates switch 206 (FIG. 2) and waits for the LED 208 (FIG. 2) to light, indicating that the 3D imaging circuitry 120 (FIG. 1) is ready for 3D imaging input. The operator then rotates the probe assembly 112 about a fixed axis through a desired angular range.

As the probe assembly 112 is rotated about the fixed axis through the desired angular range, the video capture circuitry 124 (FIG. 1) captures 2D images and the integrator 122 (FIG. 1) integrates angular velocities derived from the angle tracker 204 to obtain the relative angular position of each acquired 2D image.

Each 2D image is thus tagged with a relative angular position and saved in a buffer.

When the operator has finished a desired angular sweep about a fixed axis, he may operate switch 206 to terminate 2D image acquisition.

The acquired and duly tagged 2D images are then embedded in a 3D volume. The operator may then select regions of interest within the 3D volume, preferably in accordance with the teachings of U.S. patent applications Ser. Nos. 09/351, 252 and 09/352,002, both filed Jul. 12, 1999, the disclosure of which is hereby incorporated by reference. A 3D video image of the selected region of interest from a selected viewpoint may then be generated by conventional technique, for example as discussed in "Efficient Ray Tracing of Volume Data", by M. Levoy, ACM Transactions on Graphics, Vol. 9, No. 3, pp 245–261, 1990, the disclosure of which is hereby incorporated by reference.

Figure 6:
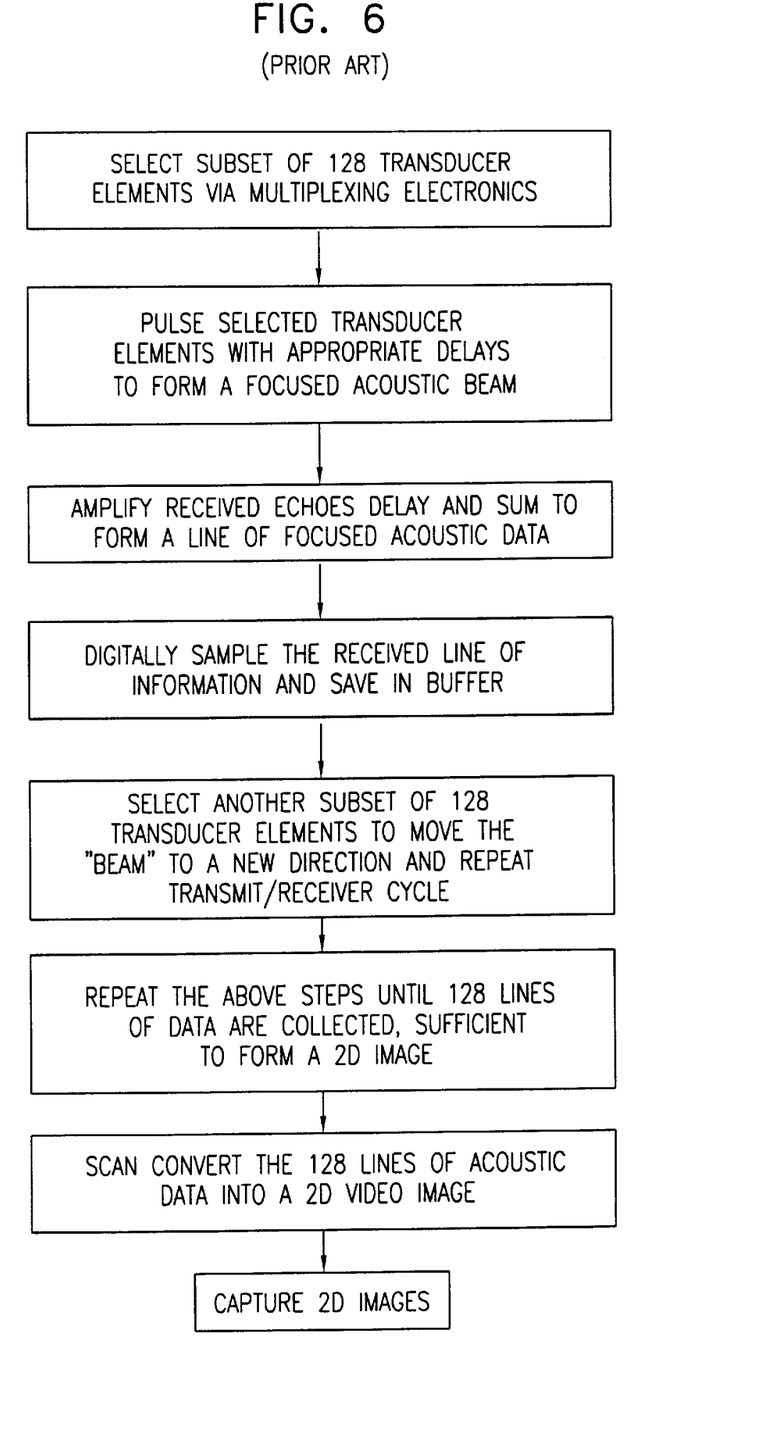
FIG. 6 is a simplified flow chart illustration of a two-dimensional image acquisition step shown in the flow chart of FIG. 5.

Reference is now made to FIG. 6, which is a simplified flow chart illustration of a typical two-dimensional image acquisition step shown in the flow chart of FIG. 5. As seen in FIG. 6, the 2D image acquisition step may be entirely conventional, as known in the prior art. Multiplexing electronics is preferably employed for selecting an appropriate subset of transducer elements. The selected transducer elements are pulsed with appropriate relative delays to form a focused acoustic beam.

The received echoes from a transmitted acoustic beam are amplified, delayed and summed to provide a spatially focused receive beam. Consecutive time samples of the receive acoustic beam form a line of image information which is stored.

The foregoing procedure is repeated for multiple different selected subsets of transducer elements until a 2D video image is built up. Appropriate 2D video images are captured, typically by circuitry 124 (FIG. 1).

Figure 7:
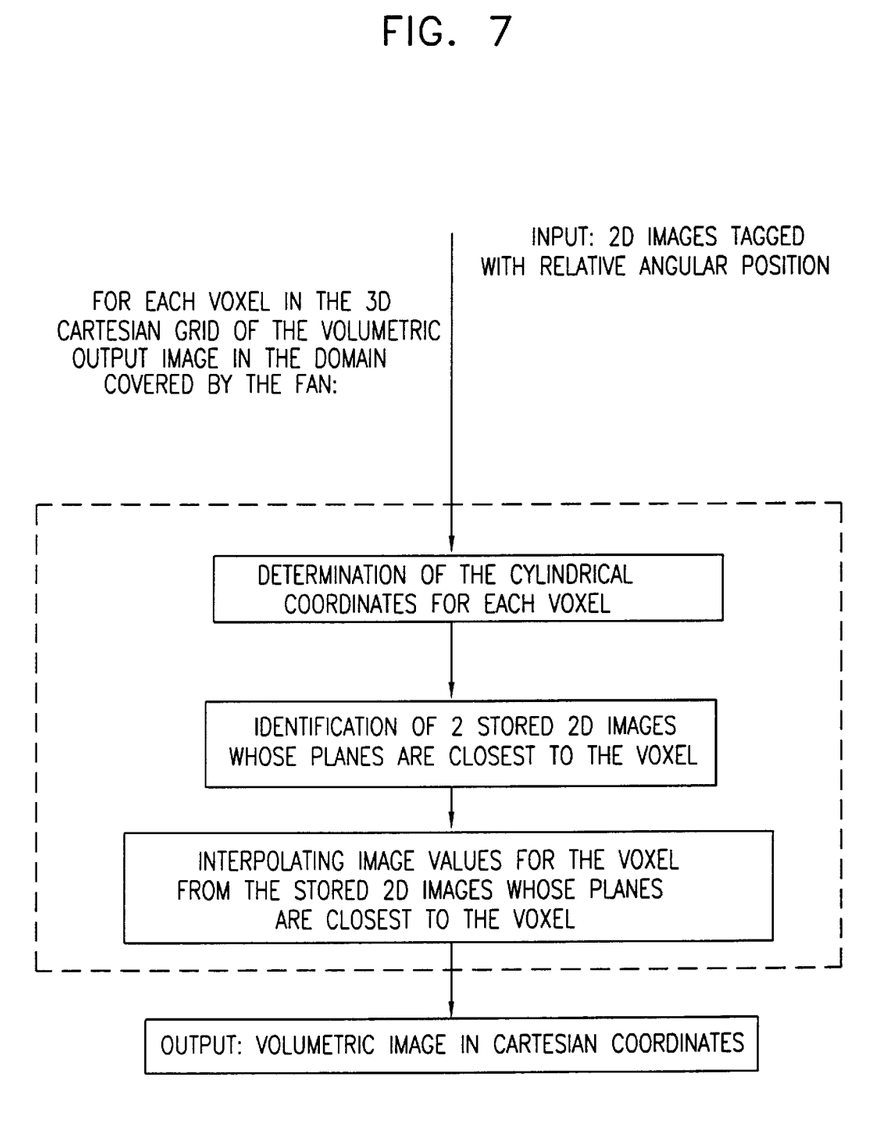
FIG. 7 is a simplified flow chart illustration of an embedding step shown in the flow chart of FIG. 5.

Reference is now made to FIG. 7, which is a simplified flow chart illustration of an embedding step shown in the flow chart of FIG. 5. The input to the functionality of FIG. 7 is a series of stored 2D images which are tagged with relative angular position information. The desired output from the functionality of FIG. 7 is a 3D volumetric image preferably defined in Cartesian coordinates which includes the volume within the patient scanned by the operator rotating the inertial probe assembly about the fixed axis through a given range of angles.

For each voxel in the 3D volumetric image, the following steps are preferably carried out:

Determination of the cylindrical coordinates for each voxel.

Identification of two stored 2D images whose planes are closest to the voxel on each of two sides thereof.

Interpolating image values for the voxel from the stored 2D images whose planes are closest to the voxel on each of two sides thereof.

Once all of the relevant voxels have been dealt with a volumetric image in Cartesian coordinates is provided and preferably stored.

Figure 8:
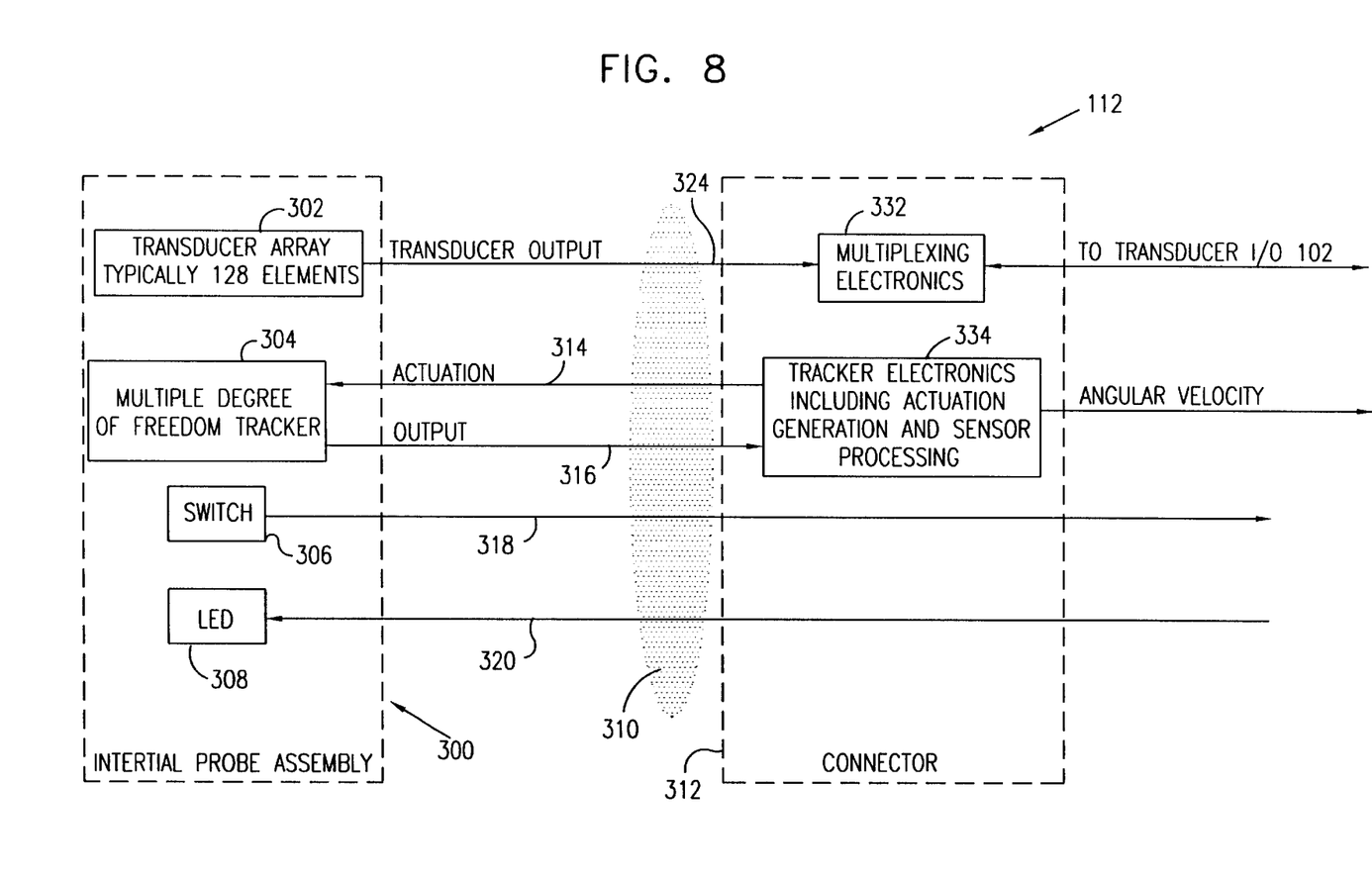
FIG. 8 is a simplified block diagram illustration of a probe assembly forming part of the system of FIG. 1 in accordance with an alternative embodiment of the present invention.

Reference is now made to FIG. 8, which is a simplified block diagram illustration of a preferred structure of a probe assembly 112 forming part of the system of FIG. 1 in accordance with another embodiment of the present invention. The probe assembly of FIG. 8 preferably includes a transducer housing 300 within which is located a conventional ultrasonic transducer array 302, such as a 128 element array which is commercially available from Sonora Medical Systems, Inc. of Longmont, Colo.

In accordance with a preferred embodiment of the present invention, there is also provided within the transducer housing 300 a multiple degree of freedom tracker 304, such as a suitable combination of multiple angle trackers, such as a Two-Axis Angular-Rate Gyro (TAARG) commercially available from Rafael of Israel and described in U.S. Pat. No. 4,930,365. This multiple degree of freedom tracker corresponds to inertial sensor 114 (FIG. 1). Alternatively, any other suitable multiple degree of freedom tracker may be employed. For example, additionally or alternatively the inertial sensor may include a micro-mechanical device. Furthermore, the inertial sensor may also include a sensor employing the Coriolis force.

Additionally located within the transducer housing 300 there may be provided a manually operable ON-OFF switch 306, which corresponds to switch 116 (FIG. 1). Preferably, a LED 308 is associated with switch 306, to indicate when switch 306 is in the ON position and thus that information provided by the multiple degree of freedom tracker 304 is being acquired. Alternatively, the LED 308 may be located elsewhere in the system. As a further alternative, any other suitable indicator may be employed.

The transducer housing 300 and its internal components are coupled via a connector cable 310 to a multifunctional connector 312. The multifunctional connector 312 is illustrated in FIG. 9 and the cable 310 is illustrated in section in FIG. 10.

Figure 9:
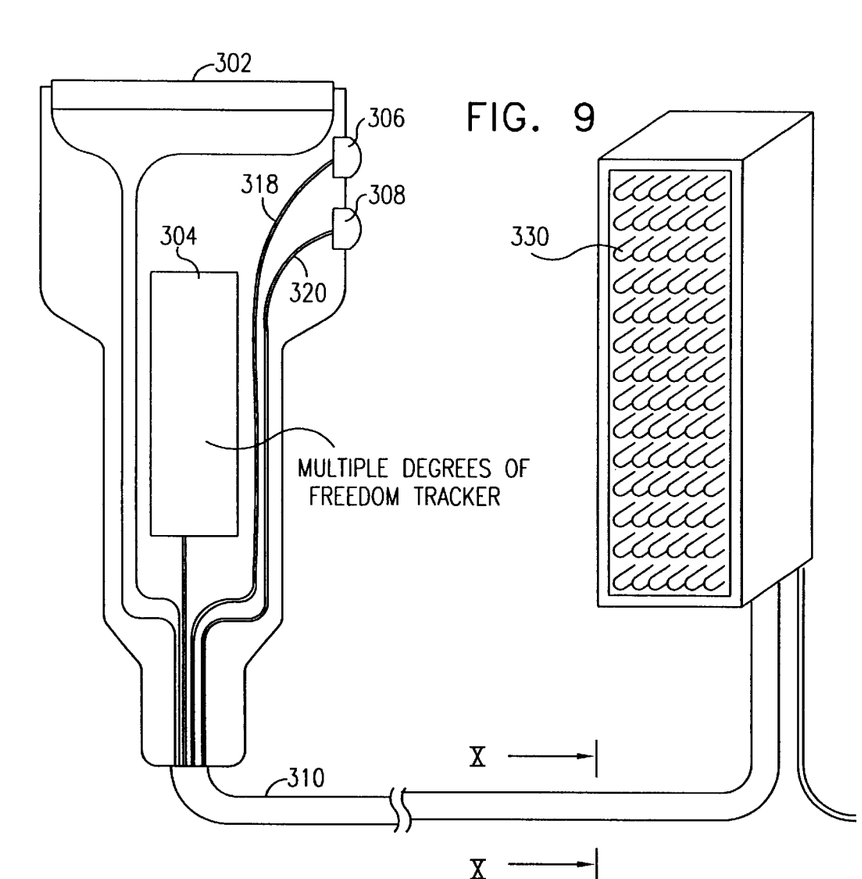
FIG. 9 is a simplified pictorial illustration of the probe assembly of FIG. 8.
Figure 10:
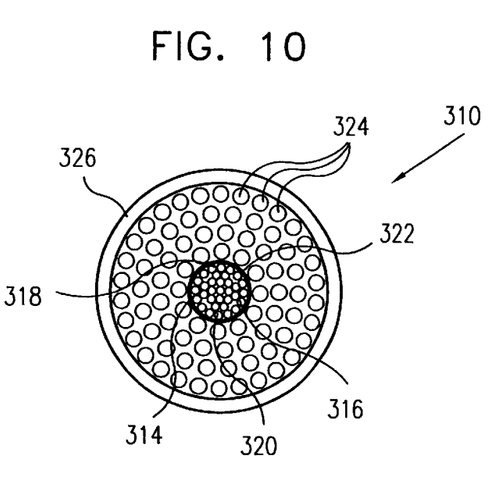
FIG. 10 is a sectional illustration of a coaxial cable forming part of the probe assembly of FIG. 8, taken along lines X—X in FIG. 8.

As seen in FIGS. 8–10, the connector cable 310 preferably includes at the interior thereof multiple degree of freedom tracker actuation and output cables 314 and 316 as well as a switch status cable 318 and a LED actuation cable 320. These cables are surrounded by a shield 322 and outwardly thereof by a collection of typically 128 transducer output cables 324 and by an outer cable shield 326. Where the switch 306 and LED 308 are not part of the probe assembly 112 (FIG. 1), cables 318 and 320 may be obviated in the connector cable 310.

Multifunctional connector 312 typically includes a 156 pin array 330, as seen in FIG. 9, which is preferably plug compatible with conventional transducer interface ports 102 (FIG. 1) of conventional system electronics 100 (FIG. 1) of conventional ultrasonic imaging systems such as Model GE 3200 manufactured by General Electric Company of the U.S.A. or a UltraMark 4+ or HDI 3000, both manufactured by ATL Inc. of Seattle, Wash., U.S.A.

As seen in FIG. 8, multifunctional connector 312 may include multiplexing electronics 332 which is usually employed in connectors which are conventionally connected to conventional transducer interface ports 102 (FIG. 1) of conventional system electronics 100 (FIG. 1) of some conventional ultrasonic imaging systems such as Model GE 3200 manufactured by General Electric Company of the U.S.A.

Multifunctional connector 312 preferably also includes tracker electronics 334 including actuation generation and sensor processing. Tracker electronics 334 suitable for use with multiple degree of freedom tracker 304 may constitute a suitable combination of tracker electronics commercially available from Rafael of Israel as part of a Two-Axis Angular-Rate Gyro (TAARG) commercially available from Rafael of Israel and described in U.S. Pat. No. 4,930,365. The output of tracker electronics 334 preferably includes an angular velocity output and other positional information, which is supplied to integrator 122 (FIG. 1).

Figure 11:
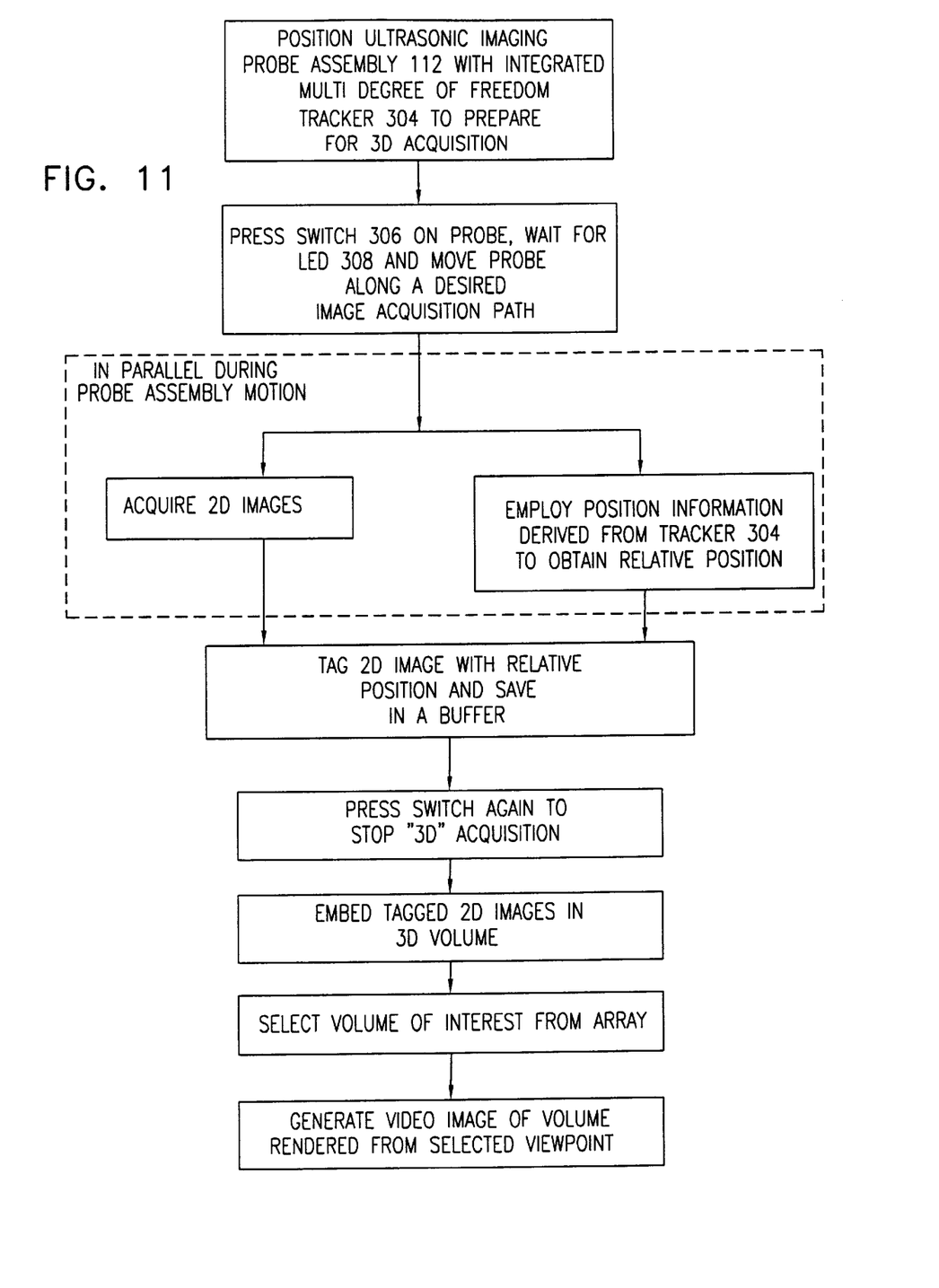
FIG. 11 is a simplified flow chart illustration of three-dimensional data acquisition in the embodiment of FIGS. 8–10.

Reference is now made to FIG. 11, which is a simplified flow chart illustration of three-dimensional data acquisition in the embodiment of FIGS. 8–10. Initially, the inertial probe assembly 112 (FIG. 1) including multiple degree of freedom tracker 304 (FIG. 8) is positioned by an operator relative to a patient for 3 dimensional image acquisition.

The operator then actuates switch 306 (FIG. 8) and waits for the LED 308 (FIG. 8) to light, indicating that the 3D imaging circuitry 120 (FIG. 1) is ready for 3D imaging input. The operator then moves the probe assembly 112 along a desired image acquisition path.

As the probe assembly of FIG. 8 is moved along the desired image acquisition path, the video capture circuitry 124 (FIG. 1) captures 2D images and the integrator 122 (FIG. 1) employs position information derived from the multiple degree of freedom tracker 304 to obtain the relative position of each acquired 2D image.

Each 2D image is thus tagged with a relative position and saved in a buffer.

When the operator has finished a desired sweep, he may operate switch 306 to terminate 3D image acquisition.

The acquired and duly tagged 2D images are then embedded in a 3D volume. The operator may then select regions of interest within the 3D volume, preferably in accordance with the teachings of U.S. patent applications Ser. Nos. 09/351, 252 and 09/352,002, both filed Jul. 12, 1999, the disclosure of which is hereby incorporated by reference. A 3D video or other image of the selected region of interest from a selected viewpoint may then be generated by conventional techniques, for example as discussed in "Efficient Ray Tracing of Volume Data", by M. Levoy, ACM Transactions on Graphics, Vol. 9, No. 3, pp 245–261, 1990, the disclosure of which is hereby incorporated by reference.

As noted above with respect to FIG. 6, the 2D image acquisition step may be entirely conventional, as known in the prior art and as described hereinabove with respect to FIG. 6.

Figure 12:
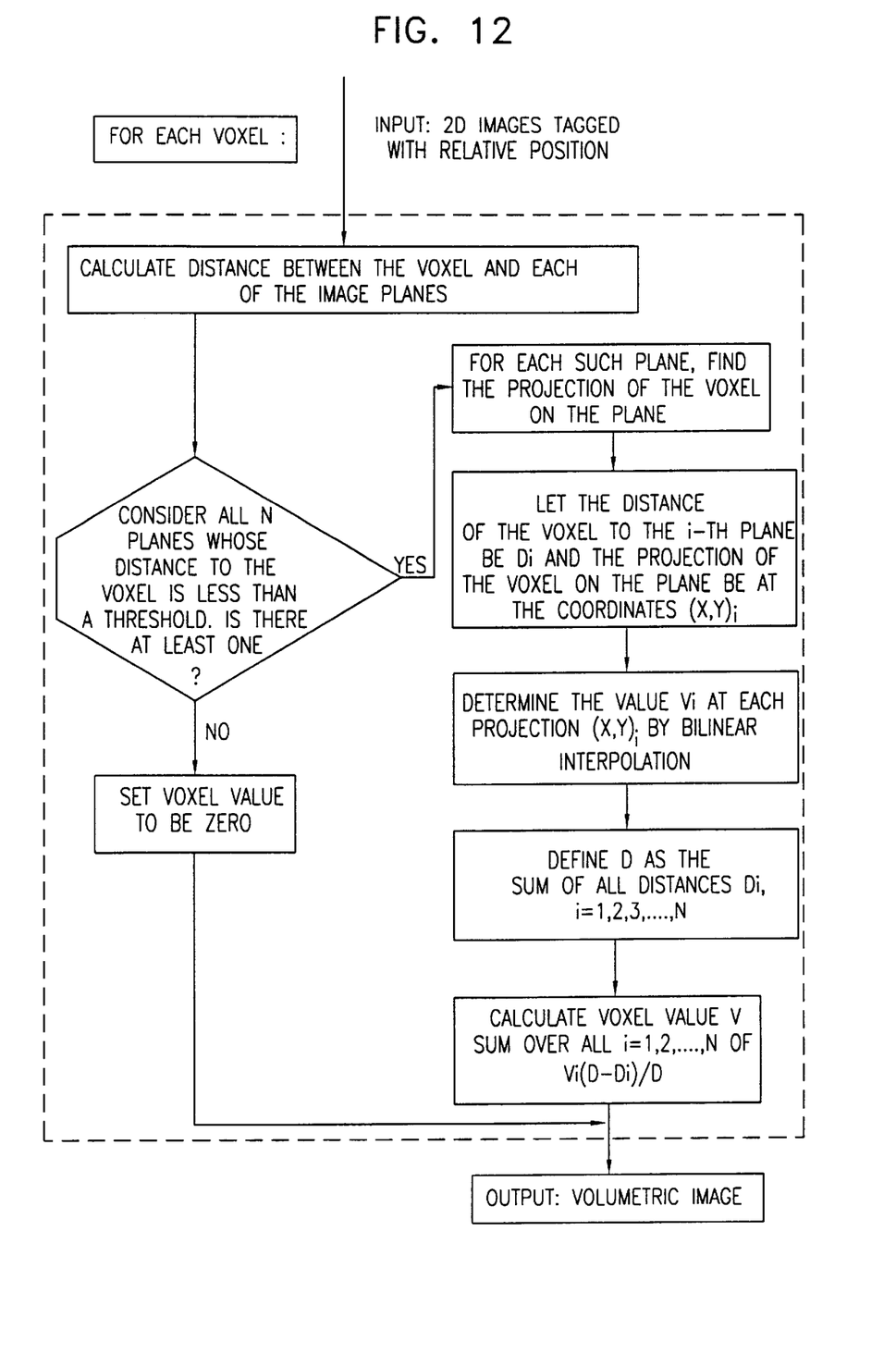
FIG. 12 is a simplified flow chart illustration of an embedding step shown in the flow chart of FIG. 11.

Reference is now made to FIG. 12, which is a simplified flow chart illustration of an embedding step shown in the flow chart of FIG. 11. The input to the functionality of FIG. 12 is a series of stored 2D images which are tagged with relative position information. The desired output from the functionality of FIG. 12 is a 3D volumetric image preferably defined in Cartesian coordinates which includes the volume within the patient scanned by the operator.

For each voxel in the 3D volumetric image, the following steps are preferably carried out:

Calculation of the distance between the voxel and the plane of each 2D image.

Consider each of the N planes whose distance to the voxel is less than a predetermined threshold distance A.

For each such plane, find the projection of the voxel on the plane.

Define the distance between each voxel to the i'th plane as Di and define the projection of the voxel on this plane as being at coordinates (x,y)i.

Determine the value Vi of each point of projection (x,y)i by bilinear interpolation.

Define D as being the sum of all distances Di, where i=1,2,3, . . . , N.

Calculate the value V for each voxel by summing Vi(D−Di)/D over i, where i=1,2,3, . . . , N.

It will be appreciated by persons skilled in the art that the present invention is not limited by what has been particularly shown and described hereinabove. Rather the scope of the present invention includes both combinations and sub-combinations of various features described hereinabove as well as modifications and variations which would occur to persons skilled in the art upon reading the foregoing description and which are not in the prior art.

What is claimed is:

1. A 3-dimensional imaging system comprising:
   a probe including:
      at least one ultrasonic transducer; and
      at least one inertial sensor; and
   electronic circuitry connected to said probe for causing said at least one ultrasonic transducer to transmit ultrasonic energy into a region and to receive reflected ultrasonic energy therefrom, creating a plurality of generally two-dimensional images whose geometrical relationship is indicated by outputs from said at least one inertial sensor, said electronic circuitry comprising image combining circuitry operative to combine information relating to said individual two-dimensional images into at least one three-dimensional image based on information from said at least one inertial sensor.

2. An ultrasonic imaging system according to claim 1 and wherein said inertial sensor comprises a gyroscope.

3. An ultrasonic imaging system according to claim 2 and wherein said gyroscope is capable of sensing motion having one degree of freedom.

4. An ultrasonic imaging system according to claim 2 and wherein said gyroscope is capable of sensing velocity having one angular degree of freedom.

5. An ultrasonic imaging system according to claim 2 and wherein said gyroscope is capable of sensing motion having more than one degree of freedom.

6. An ultrasonic imaging system according to claim 1 and wherein said inertial sensor comprises a micro-mechanical device.

7. An ultrasonic imaging system according to claim 6 and wherein said micro-mechanical device is capable of sensing motion having one degree of freedom.

8. An ultrasonic imaging system according to claim 6 and wherein said micro-mechanical device is capable of sensing velocity having one angular degree of freedom.

9. An ultrasonic imaging system according to claim 6 and wherein said micro-mechanical device is capable of sensing motion having more than one degree of freedom.

10. An ultrasonic imaging system according to claim 1 and wherein said inertial sensor comprises a sensor employing the Coriolis force.

11. An ultrasonic imaging system according to claim 10 and wherein said sensor is capable of sensing motion having one degree of freedom.

12. An ultrasonic imaging system according to claim 10 and wherein said sensor is capable of sensing velocity having one angular degree of freedom.

13. An ultrasonic imaging system according to claim 10 and wherein said sensor is capable of sensing motion having more than one degree of freedom.

14. An imaging system according to claim 1 and wherein said image combining circuitry includes video capture circuitry for capturing individual two-dimensional video images and an image organizer, combining the individual two-dimensional video images into a three-dimensional image based on information from said at least one inertial sensor.

15. An imaging system according to claim 1 and wherein said image combining circuitry includes video capture circuitry for capturing a time series of two-dimensional video images of a video stream and an image organizer, combining the individual two-dimensional video images into a three-dimensional image based on information from said at least one inertial sensor.

16. An imaging system according to claim 1 and wherein said image combining circuitry includes video capture circuitry for capturing individual two-dimensional video images, an image organizer, combining the individual two-dimensional video images into a three-dimensional image based on information from said at least one inertial sensor, and a three-dimensional visualizer receiving an output from said image organizer and providing a human sensible three-dimensional image.

17. An imaging system according to claim 1 and wherein said image combining circuitry includes video capture circuitry for capturing a time series of two-dimensional video images of a video stream, an image organizer, combining the individual two-dimensional video images into a three-dimensional image based on information from said at least one inertial sensor, and a three-dimensional visualizer receiving an output from said image organizer and providing a human sensible three-dimensional image.

18. An imaging system according to claim 1 and wherein said electronic circuitry creates said at least one three-dimensional image by interpolating image values from said individual two-dimensional ultrasonic images.

19. An ultrasonic imaging system according to claim 1 and also including an operator actuated switch for selectably operating said at least one inertial sensor.

20. An ultrasonic imaging system according to claim 19 and also including an operator sensible indicator indicating operation of said at least one inertial sensor.

21. A method for providing 3-dimensional ultrasonic imaging comprising:

providing a probe including an ultrasonic transducer and at least one inertial sensor;

causing said ultrasonic transducer to transmit ultrasonic energy into a region and to receive reflected ultrasonic radiation therefrom, creating a plurality of generally two-dimensional images;

determining a spatial relationship between the plurality of two-dimensional images using outputs from said at least one inertial sensor; and combining information relating to said individual two-dimensional images into at least one three-dimensional image based on information from said at least one inertial sensor.

22. A method for providing ultrasonic imaging according to claim 21 and wherein the step of causing includes the step of rotating the probe about a generally fixed axis at a location of interest, thereby producing a plurality of generally two dimensional images lying in planes which intersect at said axis and whose relative orientations are known from outputs of said at least one inertial sensor.

23. A method for ultrasonic imaging according to claim 21 and wherein said combining comprises capturing individual two-dimensional video images and combining the individual two-dimensional video images into a three-dimensional image based on information from said at least one inertial sensor.

24. A method for ultrasonic imaging according to claim 21 and wherein said combining comprises receiving information representing individual two-dimensional ultrasonic images and combining the individual two-dimensional ultrasonic images into a three-dimensional image based on information from said at least one inertial sensor.

25. A method for ultrasonic imaging according to claim 21 and also including operator actuation of a switch for selectably operating said at least one inertial sensor.

26. A method for ultrasonic imaging according to claim 25 and also including providing a visual indication of operation of said at least one inertial sensor.

27. A retro-fitted 2-dimensional imaging system having 3-dimensional imaging functionality comprising:

a 2-dimensional imaging probe including at least one ultrasonic transducer; and at least one inertial sensor retro-fitted to said 2-dimensional imaging probe; and electronic circuitry connected to said probe for causing said at least one ultrasonic transducer to transmit ultrasonic energy into a region and to receive reflected ultrasonic energy therefrom, creating at least one three-dimensional image.

28. An imaging system according to claim 27 and wherein said electronic circuitry includes video capture circuitry for capturing individual two-dimensional video images and an image organizer, combining the individual two-dimensional video images into a three-dimensional image based on information from said at least one inertial sensor.

29. An imaging system according to claim 27 and wherein said electronic circuitry includes video capture circuitry for capturing a time series of two-dimensional video images of a video stream and an image organizer, combining the individual two-dimensional video images into a three-dimensional image based on information from said at least one inertial sensor.

30. An imaging system according to claim 27 and wherein said electronic circuitry includes video capture circuitry for capturing individual two-dimensional video images, an image organizer, combining the individual two-dimensional video images into a three-dimensional image based on information from said at least one inertial sensor, and a three-dimensional visualizer receiving an output from said image organizer and providing a human sensible three-dimensional image.

31. An imaging system according to claim 27 and wherein said electronic circuitry includes video capture circuitry for capturing a time series of two-dimensional video images of a video stream, an image organizer, combining the individual two-dimensional video images into a three-dimensional image based on information from said at least one inertial sensor, and a three-dimensional visualizer receiving an output from said image organizer and providing a human sensible three-dimensional image.

32. An imaging system according to claim 1 and wherein said electronic circuitry creates said at least one three-dimensional image by interpolating image values from said individual two-dimensional ultrasonic images.

33. A method for providing 3-dimensional ultrasonic imaging comprising:

providing a 2-dimensional ultrasonic imaging probe including an ultrasonic transducer;

retrofitting said 2-dimensional ultrasonic imaging probe with at least one inertial sensor;

causing said ultrasonic transducer to transmit ultrasonic energy into a region and to receive reflected ultrasonic radiation therefrom, creating a plurality of generally two-dimensional images;

determining a spatial relationship between the plurality of two-dimensional images using outputs from said at least one inertial sensor; and combining information relating to said individual two-dimensional images into at least one three-dimensional image based on information from said at least one inertial sensor.

34. A method for ultrasonic imaging according to claim 33 and wherein said combining comprises capturing individual two-dimensional video images and combining the individual two-dimensional video images into a three-dimensional image based on information from said at least one inertial sensor.

35. A method for ultrasonic imaging according to claim 33 and wherein said combining comprises receiving information representing individual two-dimensional ultrasonic images and combining the individual two-dimensional ultrasonic images into a three-dimensional image based on information from said at least one inertial sensor.

* * * * *